United States Patent
Zhu et al.

(10) Patent No.: US 10,104,902 B1
(45) Date of Patent: Oct. 23, 2018

(54) HERBACEOUS SELENIUM-ENRICHED SOD NON-ANTIBIOTIC FEED AND METHOD OF MANUFACTURE THEREOF

(71) Applicant: NE PLUS ENTERPRISES, LLC, Flushing, NY (US)

(72) Inventors: Lijun Zhu, Shenzhen (CN); Lijun Qing, Shenzhen (CN); Qing Yang, Shenzhen (CN); Xiang Feng, Shenzhen (CN); Wuping Chen, Shenzhen (CN); Sixiang Chen, Shenzhen (CN)

(73) Assignee: NE PLUS ENTERPRISES, LLC, Flushing, NY (US)

( * ) Notice: Subject to any disclaimer, the term of this patent is extended or adjusted under 35 U.S.C. 154(b) by 0 days.

(21) Appl. No.: 15/644,624

(22) Filed: Jul. 7, 2017

(30) Foreign Application Priority Data

Apr. 21, 2017 (CN) .......................... 2017 1 0266296

(51) Int. Cl.
| | |
|---|---|
| A23K 20/10 | (2016.01) |
| A23K 20/26 | (2016.01) |
| A23K 50/75 | (2016.01) |
| A61K 36/06 | (2006.01) |
| A23K 20/174 | (2016.01) |
| A23K 20/189 | (2016.01) |
| A61K 35/741 | (2015.01) |
| A61K 35/747 | (2015.01) |
| A23K 20/20 | (2016.01) |
| A23K 20/142 | (2016.01) |
| A61K 35/00 | (2006.01) |

(52) U.S. Cl.
CPC .............. *A23K 20/30* (2016.05); *A23K 20/10* (2016.05); *A23K 20/142* (2016.05); *A23K 20/174* (2016.05); *A23K 20/189* (2016.05); *A23K 20/26* (2016.05); *A23K 50/75* (2016.05); *A61K 35/741* (2013.01); *A61K 35/747* (2013.01); *A61K 36/06* (2013.01); *A61K 2035/115* (2013.01)

(58) Field of Classification Search
None
See application file for complete search history.

(56) References Cited

U.S. PATENT DOCUMENTS

| | | | | |
|---|---|---|---|---|
| 8,323,708 B2 * | 12/2012 | Hartnell | ............... | A23K 20/158 |
| | | | | 426/2 |
| 2013/0022706 A1 * | 1/2013 | Bamford | ............... | A23K 1/1646 |
| | | | | 426/2 |
| 2013/0171296 A1 * | 7/2013 | Isaksen | ............... | C12N 9/2417 |
| | | | | 426/64 |
| 2015/0208693 A1 * | 7/2015 | Gilbert | ............... | C12N 9/16 |
| | | | | 424/94.6 |

FOREIGN PATENT DOCUMENTS

| | | | |
|---|---|---|---|
| CN | 102488101 A | * | 6/2012 |
| CN | 103549127 A | * | 2/2014 |
| CN | 103892134 A | * | 7/2014 |
| CN | 103907566 A | * | 7/2014 |
| CN | 105053670 A | * | 11/2015 |
| CN | 105918683 A | * | 9/2016 |

OTHER PUBLICATIONS

Xi et al. (CN 105918683A, EPO machine translation).*
Han et al. (CN 103549127A, EPO machine translation).*
Zhang et al. (CN 103907566A, WIPO machine translation).*
Chen (CN 103892134A, EPO machine translation).*
Zhang et al. (CN 103907566A, Derwent abstract).*
Xie et al. (CN 105053670A, EPO machine translation).*
Weijun (CN 102488101A, EPO machine translation).*
All About Feed, "Organic selenium is all about selenomethionine", available online at the All About Feed webpage, <<http://www.allaboutfeed.net/Feed-Additives/Articles/2015/10/Organic-selenium-is-all-about-selenomethionine-2703345W/>>, published Oct. 16, 2015.*

* cited by examiner

*Primary Examiner* — Emily A Cordas
(74) *Attorney, Agent, or Firm* — Yong Chen

(57) ABSTRACT

A non-antibiotic feed includes the following components by weight: 330-700 parts of corn, 140-230 parts of soybean meal, 80-210 parts of corn gluten meal, 35-150 parts of oil bran, 15-43 parts of rapeseed meal, 80-130 parts of wheat middling, and a feed additive. The feed additive can include various ingredients, including selenium and superoxide dismutase (SOD). The feed provides improved survival rate for poultry without using antibiotics.

1 Claim, No Drawings

HERBACEOUS SELENIUM-ENRICHED SOD NON-ANTIBIOTIC FEED AND METHOD OF MANUFACTURE THEREOF

CROSS REFERENCE TO RELATED APPLICATION

This application claims priority to Chinese patent application No. 201710266296.5, filed on Apr. 21, 2017, the disclosure of which is incorporated herein by reference in its entirety.

FIELD OF INVENTION

The invention belongs to the field of animal and poultry feeds, and in particular, relates to non-antibiotic feeds.

BACKGROUND

China has the largest capacity in the world in poultry meat production. 71% of all poultry meat consumed in China is chicken. With concepts of food safety, health, nutrition, and hygiene are better understood and accepted by the public, the level of chicken consumption will remain high for years to come.

Chickens raised in chicken farms usually live in relatively tight quarters, so a single sick chicken can infect the flock. To keep chickens healthy, antibiotics are often provided to the chickens orally or by injection. For example, antibiotics are often added in chicken feeds. However, long term use of antibiotics in chickens can inhibit growth of the poultry. Further, there has been increasing concerns of drug-resistant microorganisms that can develop in chickens with prevalent use of antibiotics. Such drug-resistant microorganisms may be transmitted to humans when the chickens are consumed.

BRIEF SUMMARY OF THE INVENTION

In one aspect, disclosed is a non-antibiotic feed comprising the following components in parts by weight: 330-700 parts of corn; 140-230 parts of soybean meal; 80-210 parts of corn gluten meal; 35-150 parts of oil bran; 15-43 parts of rapeseed meal; 80-130 parts of wheat middling; and an amount of a feed additive which comprises, by weight: 0.5-1.5 parts of choline, 0.5-1.5 parts of zeolite powder, 10-15 parts of calcium hydrogen phosphate, 1.5-4.5 parts of sodium chloride, 0.00055-0.0055 parts of selenium, 0.05-1 parts of Folium isatidis, 0.05-1 parts of isatis root, and 0.05-2 parts of superoxide dismutase (SOD). Note that any ingredients of the feed described in this application that are not corn, soybean meal, corn gluten meal, oil bran, rapeseed meal, or wheat middling are considered as components of the feed additive. Unless otherwise specified, all amounts or percentages of ingredients or materials described in this application are by weight.

In some embodiments, the feed additive accounts for 3.9%-4.1% by weight of the feed.

In some embodiments, the feed further comprises, by weight, 0.2-0.5 parts of one or more vitamins selected from the group consisting of vitamin A, vitamin B1, vitamin B2, vitamin B6, vitamin B12, vitamin C, vitamin D3, vitamin E, vitamin H, vitamin K3. In one example, the feed comprises multivitamins including vitamins A, B1, B2, B6, B12, C, D3, E, H and K3 in a ratio of: 48000000 IU:1200 mg:12000 mg:1500 mg:2500 mg:30000 mg:10000000 IU:200 mg:3000 mg.

In some embodiments, the feed further comprises, by weight, 0.1-0.3 parts of one or more enzymes selected from the group consisting of amylase, pectase, cellulase, and saccharase. In one example, the feed comprises amylase, pectase, cellulase, and saccharase in a weight ratio of 25:15:52:8.

In some embodiments, the feed further comprises, by weight, 0.5-2.5 parts of one or more mineral metals selected from the group consisting of Cu, Fe, Zn, Mn, and Co. In one example, the feed comprises Cu, Fe, Zn, Mn, and Co in a ratio of 8:90:130:130:0.2.

In some embodiments, the feed further comprises, by weight, 3.2-6.4 parts of calcium carbonate.

In some embodiments, the feed further comprises, by weight, 2.5-5.8 parts of one or more amino acids. For example, the amino acids can include 0.2-0.8 parts of threonine, 0.8-1.5 parts of methionine, and 1.5-3.5 parts lysine.

In some embodiments, the feed further comprises, by weight, 0.1-0.3 parts of Radix dichroa and 0.05-0.15 parts of Radix bupleuri.

In some embodiments, the feed further comprises, by weight, 0.02-0.08 parts of *Coptis chinensis*, 0.1-0.2 parts of Radix scutellariae, 0.05-0.15 parts of liquorice, 0.02-0.08 parts of Cortex phellodendri, and 0.02-0.08 parts of *Rheum officinale*.

In some embodiments, the selenium is in the form of an organic selenium.

In some embodiments, the feed further comprises, by weight, 0.5-1.5 parts of baking soda, 0.05-0.25 parts of phytase, and 0.01-0.08 parts of 1% iodine.

In some embodiments, the feed further comprises, by weight, 0.05-0.25 parts of probiotics. For example, the probiotics can include one or more of *lactobacillus, bacillus*, yeast, and photosynthetic bacteria. In an example, the probiotics comprises *lactobacillus, bacillus*, yeast, and photosynthetic bacteria in a weight ratio of 25:32:30:13.

In some embodiments, the feed further comprises, by weight, 0.5-2.5 parts of anti-mildew agent. In an example, the anti-mildew agent comprises sesmollient, calcium iodate, and calcium propionate in a weight ratio of 92:4:4.

In some embodiments, the feed further comprises ethoxyquin. In one example, the feed comprises, by weight, 0.05-0.25 parts of ethoxyquin.

In some embodiments, the feed comprises the following components by weight: 480 parts of corn; 150 parts of soybean meal; 120 parts of corn gluten meal; 80 parts of oil bran; 30 parts of rapeseed meal; 100 parts of wheat middling; 0.14 parts of compound enzymes including amylase, pectase, cellulase, and saccharase in a weight ratio of 25:15:52:8; 0.09 parts of probiotics including *lactobacillus, bacillus*, yeast, and photosynthetic bacteria in a weight ratio of 25:32:30:13; 0.09 parts of ethoxyquin; 0.56 parts of threonine; 1.26 parts of methionine; 2.1 parts of lysine; 0.76 parts of choline; 0.95 parts of zeolite powder; 12.06 parts of calcium hydrogen phosphate; 1.83 parts of mineral metal elements including Cu, Fe, Zn, Mn, and Co in a weight ratio of 8:90:130:130:0.2; 2.85 parts of sodium chloride; 1.28 parts of an anti-mildew agent including sesmollient, calcium iodate, and calcium propionate in a weight ratio of 92:4:4; 0.5 parts of SOD; 0.000825 parts of selenium; 0.25 parts of Folium isatidis; 0.25 parts of isatis root; 0.04 parts of 1% iodine; 0.11 parts of phytase; 0.95 parts of baking soda; 0.2 parts of Radix dichroa; 0.08 parts of Radix bupleuri; 0.04 parts of *Coptis chinensis;* 0.15 parts of Radix scutellariae; 0.08 parts of liquorice; 0.06 parts of Cortex phellodendri; and 0.05 parts of *Rheum officinale*.

In another aspect, the present invention provides a method for preparing a feed disclosed herein. The method includes: (a) mixing the corn, soybean meal, corn gluten meal, oil bran, rapeseed meal and wheat middling according to the amounts described herein with water evenly to obtain a first mixture; (b) heating the first mixture to 40-60° C. while stirring to obtain a feed base; (c) adding a feed additive described herein to the feed base obtained in (b) while stirring the feed base; and (d) upon completion of the addition of the feed additive, further stirring the mixture of the feed base and the feed additive to obtain the feed.

DETAILED DESCRIPTION OF THE INVENTION

The technical problem to be solved by the invention is to provide a non-antibiotic feed free of penicillin, sulfonamides, florfenicol, chloramphenicol and other drugs.

To achieve such purpose, in one aspect, the present invention provides a non-antibiotic (or antibiotic-free) feed comprising corn, soybean meal, corn gluten meal, oil bran, rapeseed meal, and wheat middling, and a feed additive. As used herein, corn, soybean meal, corn gluten meal, oil bran, rapeseed meal, and wheat middling constitutes a feed base, and all other ingredients in the feed which are not corn, soybean meal, corn gluten meal, oil bran, rapeseed meal, or wheat middling are considered as components of the feed additive.

In some embodiments, the present invention provides a non-antibiotic feed that comprises in parts by weight: 330-700 parts of corn; 140-230 parts of soybean meal; 80-210 parts of corn gluten meal; 35-150 parts of oil bran; 15-43 parts of rapeseed meal; 80-130 parts of wheat middling, 0.5-1.5 parts of choline, 0.5-1.5 parts of zeolite powder, 10-15 parts of calcium hydrogen phosphate, 1.5-4.5 parts of sodium chloride, 0.00055-0.0055 parts of selenium, 0.05-1 parts of Folium isatidis, 0.05-1 parts of isatis root, and 0.05-2 parts of superoxide dismutase (SOD).

In some embodiments, the feed further comprises, by weight, 0.1-0.3 parts of one or more enzymes selected from the group consisting of amylase, pectase, cellulase, saccharase. In one example, the feed further comprises amylase, pectase, cellulase, and saccharase in a weight ratio of 25:15:52:8.

In some embodiments, the feed further comprises one or more mineral metal elements selected from the group consisting of Cu, Fe, Zn, Mn, and Co. In some embodiments, the feed comprises, by weight, 0.5-2.5 parts of one or more mineral metal elements. In one example, the feed comprises mineral metal elements Cu, Fe, Zn, Mn, and Co in a ratio of 8:90:130:130:0.2.

In some embodiments, the feed further comprises, by weight, 3.2-6.4 parts of calcium carbonate. The calcium carbonate can be added in the form of a stone powder, which contains about 32% of calcium carbonate.

In some embodiments, the feed further comprises, by weight, 2.5-5.8 parts of one or more amino acids. For example, the amino acids can include 0.2-0.8 parts of threonine, 0.8-1.5 parts of methionine, and 1.5-3.5 parts lysine.

In some embodiments, the feed further comprises, by weight, 0.1-0.3 parts of Radix dichroa and 0.05-0.15 parts of Radix bupleuri.

In some embodiments, the feed further comprises, by weight: 0.02-0.08 parts of *Coptis chinensis*, 0.1-0.2 parts of Radix scutellariae, 0.05-0.15 parts of liquorice, 0.02-0.08 parts of Cortex phellodendri, and 0.02-0.08 parts of *Rheum officinale*.

In some embodiments, the feed further comprises, by weight: 0.5-1.5 parts of baking soda, 0.05-0.25 parts of phytase, and 0.01-0.08 parts of 1% iodine.

In some embodiments, the feed further comprises, by weight, 0.05-0.25 parts of probiotics. For example, the probiotics can include one or more of *lactobacillus, bacillus*, yeast, and photosynthetic bacteria. In an example, the probiotics comprises *lactobacillus, bacillus*, yeast, and photosynthetic bacteria in a weight ratio of 25:32:30:13.

In some embodiments, the feed can further include an anti-mildew agent. For example, the anti-mildew agent can include one or more of sesmollient, calcium iodate, and calcium propionate. In some embodiments, the feed comprises, by weight, 0.5-2.5 parts of the anti-mildew agent. In one example, the weight percentage or ratio of sesmollient, calcium iodate, and calcium propionate in the anti-mildew agent can be 92:4:4.

In some embodiments, the feed further comprises one or more vitamins selected from the group consisting of vitamin A, vitamin B1, vitamin B2, vitamin B6, vitamin B12, vitamin C, vitamin D3, vitamin E, vitamin H, vitamin K3. In some embodiments, the feed comprises, by weight, 0.2-0.5 parts of one or more vitamins. In one example, these vitamins can be added in a ratio of: 48000000 IU:1200 mg:12000 mg:1500 mg:2500 mg:30000 mg:10000000 IU:200 mg:3000 mg.

In some embodiments, the feed further comprises ethoxyquin as an antioxidant.

In some embodiments, the feed additive accounts for about 3.9%-4.1% by weight of the feed.

In some embodiments, the selenium can be in the form of an organic selenium. For example, the selenium may be complexed with an amino acid, e.g., L-selenomethionine. In some embodiments, the organic selenium may be derived from a fungus, e.g., Pleurotus ostreatus. For example, Pleurotus ostreatus can be cultivated for 45 days, dried and ground, placed into a Soxhlet extractor, which was added with ethanol. The extraction is performed over a water bath, and a white powdery product is obtained which contains selenium.

In some embodiments, the SOD is a powdery product and has activity of about 10,000 units/g or greater. For example, the SOD can have an activity of 300,000 units/g.

In some embodiments, the vitamins, enzymes, probiotics, antioxidants, amino acids, choline, zeolite powder, calcium hydrogen phosphate, mineral metal elements, sodium chloride, baking soda, anti-mildew agent, SOD, selenium, Folium isatidis, and isatis root are in solid form.

In some embodiments, to prepare the feed additive of the present invention, the Folium isatidis, and isatis root can be first mixed and grounded to form a mixture. The mixture can then be mixed with sodium chloride, baking soda, anti-mildew agent and other components to obtain the feed additive.

In some embodiments, the weight ratio of Folium isatidis to isatis root can be 1:1. The Folium isatidis and the isatis root can be mixed at a 1:1 ratio and ground together. Then 0.1-2 parts of the mixture of the Folium isatidis and the isatis root can be used to make the feed additive. The mixture of the Folium isatidis and the isatis root preferably accounts for 0.2-1.2 parts in the feed, and the effect is optimal when the mixture of the Folium isatidis and the isatis root accounts for 0.5 parts, that is, each of the Folium isatidis and the isatis root accounts for 0.25 parts.

In some specific embodiments, the feed comprises the following components in parts by weight: 480 parts of corn, 150 parts of soybean meal, 120 parts of corn gluten meal, 80 parts of oil bran, 30 parts of rapeseed meal, 100 parts of wheat middling, 0.14 parts of compound enzymes including amylase, pectase, cellulase, and saccharase in a weight ratio of 25:15:52:8; 0.09 parts of probiotics including *lactobacillus, bacillus*, yeast, and photosynthetic bacteria in a weight ratio of 25:32:30:13; 0.09 parts of ethoxyquin; 0.56 parts of threonine; 1.26 parts of methionine; 2.1 parts of lysine; 0.76 parts of choline; 0.95 parts of zeolite powder; 12.06 parts of calcium hydrogen phosphate; 1.83 parts of mineral metal elements including Cu, Fe, Zn, Mn, and Co in a weight ratio of 8:90:130:130:0.2; 2.85 parts of sodium chloride; 1.28 parts of an anti-mildew agent including sesmollient, calcium iodate, and calcium propionate in a weight ratio of 92:4:4; 0.5 parts of SOD; 0.000825 parts of selenium; 0.25 parts of Folium isatidis; 0.25 parts of isatis root; 0.04 parts of 1% iodine; 0.11 parts of phytase; 0.95 parts of baking soda; 0.2 parts of Radix dichroa; 0.08 parts of Radix bupleuri; 0.04 parts of *Coptis chinensis;* 0.15 parts of Radix scutellariae; 0.08 parts of liquorice; 0.06 parts of Cortex phellodendri; and 0.05 parts of *Rheum officinale*.

In some embodiments, a method of preparing the non-antibiotic feed comprises the following steps: (a) mixing the corn, soybean meal, corn gluten meal, oil bran, rapeseed meal and wheat middling according to the ratios described herein with water evenly to obtain a first mixture; heating the first mixture to 40-60° C. while stirring to obtain a feed base; adding the feed additive described herein to the feed base while stirring the feed base; and after completion of the addition of the feed additive, further stirring the mixture of the feed base and the feed additive for additional time, e.g., 1-2 minutes, to obtain the feed.

Embodiments disclosed herein have the following beneficial effects:

The feed of the present disclosure does not contain antibiotics. The meat product of poultry contains no antibiotics. Sample chicken was inspected by the Institute of Veterinary Drug and Feed Control of Hunan Province, China (Hunan Livestock and Poultry Aquatic Product Quality Inspection and Testing Center). Nitrofurans, sulfonamides, oxytetracycline, chlortetracycline, tetracycline, doxycycline, enrofloxacin, Ciprofloxacin, florfenicolamine, arsenic, lead and the like were not detected.

By using the feed, the quality of poultry meat products can achieve or exceed the quality of free-range poultry or even wild poultry. The meat of the poultry fed by the disclosed feed is tender, not greasy, has no fishy smell, needs less seasoning during cooking and tastes better.

In some experiments, chickens fed by the feed of the present invention demonstrated excellent absorption of nutrition and low incidents of disease.

In some examples, the calcium hydrogen phosphate, mineral metal elements, multivitamins, baking soda, probiotics, choline and other nutrients are added to achieve a synergistic effect. The accumulation of harmful substances in the livestock and poultry can be reduced, the survival rate improved, egg production of the poultry improved, intestinal peristalsis promoted. The incidence of intestinal diseases can be controlled, diarrhea and anemia of livestock and poultry can be effectively prevented, the metabolism adjusting capability and anti-stress capability of the livestock and poultry can be enhanced, the overall immunity of the livestock and poultry can be improved, the resistance to diseases can be enhanced, digestive diseases can be significantly reduced. Poultry fed with the feed of the present invention had red crest, and bright and smooth feathers.

In some examples, Radix dichroa, Radix bupleuri and SOD are synergistically combined, which can help prevent chicken coccidiosisthe. In some examples, Radix scutellariae, Folium isatidis and isatis root are synergistically combined, which can help prevent chicken white diarrhea. The feed successfully solved the problem of recurrence of white diarrhea and chicken coccidiosis when antibiotics are used.

SOD can effectively scavenge free radicals that damage healthy cells, and delay cell aging. Organic selenium can enhance immunity, and promote absorption to isatis root, Folium isatidis, *Coptis chinensis*, licorice and other herbs. The isatis root and Folium isatidis can detoxify the body and prevent diseases. The combined use of various materials such as SOD, enzymes, organic selenium, isatis root, Folium isatidis, *Coptis chinensis* and licorice can achieve a better synergistic effect and improve the absorption efficiency of nutrients for the livestock and poultry, thereby improving the feed conversion rate by 10-20%, shortening the feeding period for growth, saving feed, and lowering cost.

In some examples, the antioxidant used in the feed can prevent the oxidative degradation of the vitamins and other nutrients, the anti-mildew agent can prevent the mildew formation, and the combination of the antioxidant and anti-mildew agent work to improve the stability of the feed of the invention.

It is easy to use the feed of the present invention. For example, it can be mixed with water having at a temperature of 40-60° C., which is beneficial to the absorption of the SOD and various enzymes.

In some examples, the combination of licorice and SOD in the feed can make chicken meet taste sweet and delicious.

In some examples, the combination of corn and corn gluten meal can make the fat deposit in the chicken skin to have a golden color, and promote the chicken growth as well as increase the feed utilization rate.

In order to enable those skilled in the art to better understand the technical solutions of the invention, the invention is described in further detail with the Examples below with reference to the drawings. The Examples are merely illustrative and explanatory and should not be construed as limiting the scope of the invention.

Example 1

A non-antibiotic feed includes the following components in parts by weight: 700 parts of corn, 230 parts of soybean meal, 210 parts of corn gluten meal, 150 parts of oil bran, 43 parts of rapeseed meal, 130 parts of wheat middling, and an amount of a feed additive. The amount of the feed additive constitutes about 4.10% (by weight) of the feed, and includes by weight: 0.25 parts of phytase, 0.08 parts of 1% iodine, 1.5 parts of baking soda, 0.5 parts of multivitamins (including vitamins A, B1, B2, B6, B12, C, D3, E, H, K3 in a ratio of 48000000 IU:1200 mg:12000 mg:1500 mg:2500 mg:30000 mg:10000000 IU:200 mg:3000 mg), 0.3 parts of compound enzymes (including amylase, pectase, cellulase, and saccharase in a weight ratio of 25:15:52:8), 0.25 parts of probiotics (containing *lactobacillus, bacillus*, yeast, and photosynthetic bacteria in a weight ratio of 25:32:30:13), 0.25 parts of ethoxyquin, 5.8 parts of amino acids (including 0.8 parts of threonine, 1.5 parts of methionine, and 3.5 parts of lysine), 1.5 parts of choline, 1.5 parts of zeolite powder, 15 parts of calcium hydrogen phosphate, 2.5 parts of mineral metal elements (including Cu, Fe, Zn, Mn, and Co in a ratio of 8:90:130:130:0.2); 4.5 parts of sodium chloride, 2.5 parts of anti-mildew agent (including sesmollient, calcium iodate, and calcium propionate in a weight ratio of 92:4:4), 20 parts of stone powder (containing 6.4 parts of calcium carbonate), 2 parts of SOD, 0.0055 parts of selenium, 1 parts of Folium isatidis, 1 parts of isatis root, 0.3 parts of Radix dichroa, 0.15 parts of Radix bupleuri, 0.08 parts of *Coptis chinensis*, 0.2 parts of Radix scutellariae, 0.15 parts of liquorice, 0.08 parts of Cortex phellodendri, and 0.08 parts of *Rheum officinale*.

The preparation method of the feed described in this Example comprises the following steps:

Step 1: evenly mixing the corn, soybean meal, corn gluten meal, oil bran, rapeseed meal and wheat middling according to the ratios provided herein, adding an amount of water, stirring thoroughly, and heating to 60° C. while stirring to obtain a feed base;

Step 2: adding the feed additive to the feed base obtained in Step 1 while stirring, and further stirring for 2 min after the addition is completed to obtain the non-antibiotic feed.

Example 2

A non-antibiotic feed includes the following components in parts by weight: 330 parts of corn, 140 parts of soybean meal, 80 parts of corn gluten meal, 35 parts of oil bran, 15 parts of rapeseed meal, 80 parts of wheat middling, and an amount of a feed additive. The amount of feed additive constitutes about 3.9% (by weight) of the feed, and includes, by weight: 0.01 parts of 1% iodine, 0.5 parts of baking soda and 0.05 parts of phytase, 0.2 parts of multivitamins (including vitamins A, B1, B2, B6, B12, C, D3, E, H, K3 in a ratio of 48000000 IU:1200 mg:12000 mg:1500 mg:2500 mg:30000 mg:10000000 IU:200 mg:3000 mg), 0.1 parts of compound enzymes (including amylase, pectase, cellulase, and saccharase in a weight ratio of 25:15:52:8), 0.05 parts of probiotics (including *lactobacillus, bacillus*, yeast, and photosynthetic bacteria in a weight ratio of 25:32:30:13), 0.05 parts of ethoxyquin, 0.2 parts of threonine, 0.8 parts of methionine, 1.5 parts of lysine, 0.5 parts of choline, 0.5 parts of zeolite powder, 10 parts of calcium hydrogen phosphate, 0.5 parts of mineral metal elements (including Cu, Fe, Zn, Mn, and Co in a ratio of 8:90:130:130:0.2), 1.5 parts of sodium chloride, 0.5 parts of an anti-mildew agent (including sesmollient, calcium iodate, and calcium propionate in a weight ratio of 92:4:4), 10 parts of stone powder (containing 3.2 parts of calcium carbonate), 0.05 parts of SOD, 0.00055 parts of selenium, 0.05 parts of Folium isatidis, 0.05 parts of isatis root, 0.1 parts of Radix dichroa, 0.05 parts of Radix bupleuri, 0.02 parts of *Coptis chinensis*, 0.1 parts of Radix scutellariae, 0.05 parts of liquorice, 0.02 parts of Cortex phellodendri, and 0.02 parts of *Rheum officinale*.

The preparation method of the feed in the Example 2 comprises the following steps:

Step 1: evenly mixing the corn, soybean meal, corn gluten meal, oil bran, rapeseed meal and wheat middling according to the ratios provided herein, adding an amount of water, stirring thoroughly, and heating to 40° C. while stirring to get a feed base; and Step 2: adding the feed additive to the feed base obtained in the Step 1 while stirring, and further stirring for 1 min after addition is completed to obtain the non-antibiotic feed.

The feed obtained in Example 2 was inspected by the Hunan Province Institute of Veterinary Drug and Feed Control (Hunan Livestock and Poultry Aquatic Product Quality Inspection and Testing Center). The inspection report is shown in Table 1.

TABLE 1

| Item | Unit | Reference Standard | Measured Value | Evaluation |
|---|---|---|---|---|
| Aspartic acid | % | / | 1.62 | / |
| Threonine | % | / | 0.83 | / |
| Serine | % | / | 1.06 | / |
| Glutamic acid | % | / | 4.95 | / |
| Glycine | % | / | 0.79 | / |
| Alanine | % | / | 1.32 | / |
| Valine | % | / | 0.94 | / |
| Isoleucine | % | / | 0.81 | / |
| Leucine | % | / | 2.27 | / |
| Tyrosin | % | / | 0.81 | / |
| Phenylalanine | % | / | 1.06 | / |
| Lysine | % | / | 1.03 | / |
| Histidine | % | / | 0.69 | / |
| Arginine | % | / | 0.99 | / |
| Proline | % | / | 1.55 | / |
| Crude protein | % | / | 18.4 | / |
| Clenbuterol hydrochloride | mg/kg | / | not detected (*<0.0005) | / |
| Melamine | mg/kg | / | not detected (*<2.0) | / |
| Chloramphenicol | mg/kg | / | not detected (*<0.01) | / |
| Sulfamethazine | mg/kg | / | not detected (*<0.002) | / |
| Sulfadiazine | mg/kg | / | not detected (*<0.005) | / |
| Sulfamethoxazole | mg/kg | / | not detected (*<0.002) | / |
| Sulfamonomethoxine | mg/kg | / | not detected (*<0.005) | / |
| Sulfaquinoxaline | mg/kg | / | not detected (*<0.002) | / |

Example 3

A non-antibiotic feed includes the following components in parts by weight: 480 parts of corn, 150 parts of soybean meal, 120 parts of corn gluten meal, 80 parts of oil bran, 30 parts of rapeseed meal, 100 parts of wheat middling, and an amount of a feed additive. The amount of feed additive constitutes about 4.0% (by weight) of the feed, and includes, by weight: 0.04 parts of 1% iodine, 0.11 parts of phytase, and 0.95 parts of baking soda, 0.31 parts of multivitamins (including vitamins A, B1, B2, B6, B12, C, D3, E, H, K3 in a ratio of 48000000 IU:1200 mg:12000 mg:1500 mg:2500 mg:30000 mg:10000000 IU:200 mg:3000 mg), 0.14 parts of compound enzymes (including amylase, pectase, cellulase, and saccharase in a weight ratio of 25:15:52:8), 0.09 parts of probiotics (including *lactobacillus, bacillus*, yeast, and photosynthetic bacteria in a weight ratio of 25:32:30:13), 0.09 parts of ethoxyquin, 0.56 parts of threonine, 1.26 parts of methionine, 2.1 parts of lysine, 0.76 parts of choline, 0.95 parts of zeolite powder, 12.06 parts of calcium hydrogen phosphate, 1.83 parts of mineral metal elements (including Cu, Fe, Zn, Mn, and Co in a ratio of 8:90:130:130:0.2), 2.85 parts of sodium chloride, 1.28 parts of an anti-mildew agent (including sesmollient, calcium iodate, and calcium propionate in a weight ratio of 92:4:4), 13.34 parts of stone powder (containing 4.27 parts of calcium carbonate), 0.5 parts of SOD, 0.000825 parts of selenium, 0.25 parts of Folium isatidis, 0.25 parts of isatis root, 0.2 parts of Radix dichroa, 0.08 parts of Radix bupleuri, 0.04 parts of *Coptis chinensis*, 0.15 parts of Radix scutellariae, 0.08 parts of liquorice, 0.06 parts of Cortex phellodendri, and 0.05 parts of *Rheum officinale*.

The preparation method of the feed in this Example comprises the following steps:

Step 1: evenly mixing the corn, soybean meal, corn gluten meal, oil bran, rapeseed meal and wheat middling according to the ratios provided herein, adding an amount of water, stirring thoroughly, and heating to 45° C. while stirring to obtain a feed base; and Step 2: adding the feed additive to the feed base obtained in the Step 1 while stirring, and further stirring for 1.5 min after addition is completed to obtain the non-antibiotic feed.

The feed obtained in the Example 3 was used to carry out feeding tests for chickens. Three different breeds of chickens were obtained from local chicken suppliers. Each breed of chickens was separated into five groups, three test groups and two control groups, each group having 20 chickens. All chickens were raised in a standard chicken farm with controlled temperature, humidity and other standard environmental conditions. The chickens in the test groups were fed with the feed obtained in Example 3, whereas the chickens in the control groups were fed with a commercial feed. In the first 12 days, antibiotics such as Amoxicillin, Florfenicol were added in the commercial feed, whereas between day 12-45 Sulfonamides were added in the commercial feed for reducing mortality caused by infectious diseases.

In the test chicken groups, the percentage of chicken catching white diarrhea was about 15% within 10 days, and 1% died of white diarrhea. In contrast, in the control groups, the percentages of chicken catching white diarrhea were 20%-25% within 10 days and 3%-5% died of white diarrhea.

In the test chicken groups, no chicken was infected with coccidian disease during days 11-45 and no chicken died of coccidian disease. In contrast, in the control groups, the percentages of chicken catching coccidian disease were 10%-18% during days 11-45, and 1%-5% of the chicken died of coccidian disease.

In the test chicken groups, no chickens were infected with other diseases. In contrast, in the control groups, some chickens were infected with *E. Coli* and infectious bronchitis.

The meat of test chickens was also inspected by the Hunan Province Institute of Veterinary Drug and Feed Control (Hunan Livestock and Poultry Aquatic Product Quality Inspection and Testing Center). The inspection report is shown in Table 2. Nitrofurans, sulfonamides, oxytetracycline, chlortetracycline, tetracycline, doxycycline, enrofloxacin, Ciprofloxacin, florfenicolamine, arsenic, lead and the like were not detected in the meat of test chickens.

TABLE 2

| Item | Unit | Reference Standard | Measured Value | Evaluation |
|---|---|---|---|---|
| Nitrofurans | mg/kg | Non-detect (ND) | ND | In compliance |
| AOZ | mg/kg | / | ND (*<0.0005) | / |
| AMOZ | mg/kg | / | ND (*<0.0005) | / |
| AHD | mg/kg | / | ND (*<0.0005) | / |
| SEM | mg/kg | / | ND (*<0.0005) | / |
| Sulfonamides | mg/kg | <0.1 | ND (*<0.0005) | In compliance |
| SM2 | mg/kg | / | ND (*<0.0005) | / |
| SMM | mg/kg | / | ND (*<0.0005) | / |
| SDM | mg/kg | / | ND (*<0.0005) | / |
| SMZ | mg/kg | / | ND (*<0.0005) | / |
| SQ | mg/kg | / | ND (*<0.0005) | / |
| Terramycin | mg/kg | <0.1 | ND (*<0.05) | In compliance |
| Aureomycin | mg/kg | / | ND (*<0.05) | / |
| Tetracycline | mg/kg | / | ND (*<0.05) | / |
| Deoxytetracycline | mg/kg | <0.1 | ND (*<0.05) | In compliance |
| enrofloxacin | mg/kg | <0.1 | ND (*<0.02) | In compliance |
| Ciprofloxacin | mg/kg | / | ND (*<0.02) | / |
| Florfenicol | mg/kg | <0.1 | ND (*<0.001) | In compliance |
| Florfenicol amine | mg/kg | / | ND (*<0.001) | / |
| Total arsenic | mg/kg | <0.5 | 0.025 | In compliance |
| Lead | mg/kg | <0.2 | ND (*<0.005) | In compliance |

The SOD content in the test chicken serum was detected to be about 185 U/mL by intravenous blood collection. In contract, the serum SOD content in the control chicken was about 80 U/mL.

It is to be understood that the terms "comprise", "include" or any other variants thereof are intended to cover non-exclusive inclusion, in such way that the processes, methods, products or equipment comprising a series of elements include not only those elements, but also other elements that are not explicitly listed, or elements that are inherent to such processes, methods, products, or equipment.

The principles and embodiments of the invention have been described by way of examples, and the description of the examples and specific embodiments is merely used to illustrate the core concepts of the invention. Without departing from the principles of the invention, improvements, modifications, or variations can be made or the technical features disclosed can be combined in a manner which is apparent to skilled artisans in the art. These improvements, modifications, variations or combinations are within the scope of the invention.

What is claimed is:

1. A non-antibiotic feed, comprising the following components by weight:
    480 parts of corn;
    150 parts of soybean meal;
    120 parts of corn gluten meal;
    80 parts of oil bran;
    30 parts of rapeseed meal;
    100 parts of wheat middling;
    0.14 parts of compound enzymes including amylase, pectase, cellulase, and saccharase in a weight ratio of 25:15:52:8;
    0.09 parts of probiotics including *Lactobacillus, Bacillus*, yeast, and photosynthetic bacteria in a weight ratio of 25:32:30:13;
    0.09 parts of ethoxyquin;
    0.56 parts of threonine;
    1.26 parts of methionine;
    2.1 parts of lysine;
    0.76 parts of choline;
    0.95 parts of zeolite powder;

12.06 parts of calcium hydrogen phosphate;
1.83 parts of mineral metal elements including Cu, Fe, Zn, Mn, and Co in a weight ratio of 8:90:130:130:0.2;
2.85 parts of sodium chloride;
1.28 parts of an anti-mildew agent;
0.5 parts of superoxide dismutase (SOD);
0.000825 parts of selenium;
0.25 parts of Folium isatidis;
0.25 parts of isatis root;
0.04 parts of 1% iodine;
0.11 parts of phytase;
0.95 parts of baking soda;
0.2 parts of Radix dichroa;
0.08 parts of Radix bupleuri;
0.04 parts of *Coptis chinensis;*
0.15 parts of Radix scutellariae;
0.08 parts of liquorice;
0.06 parts of Cortex phellodendri; and
0.05 parts of *Rheum officinale,*
wherein the non-antibiotic feed, when fed to chickens, is effective for preventing white diarrhea and coccidiosis in the chickens.

* * * * *